United States Patent [19]

Bisaha et al.

[11] Patent Number: 5,610,158

[45] Date of Patent: Mar. 11, 1997

[54] 4-OXO- AND 4H-IMIDAZO(5,1-C)(1,4)BENZOXAZINES USEFUL AS BENZODIAZEPINE RECEPTOR-BINDING AGENTS

[75] Inventors: Sharon N. Bisaha, Titusville, N.J.; Ronald B. Gammill, Portage, Mich.

[73] Assignee: The Upjohn Company, Kalamazoo, Mich.

[21] Appl. No.: 285,560

[22] Filed: Aug. 3, 1994

Related U.S. Application Data

[63] Continuation of PCT/US93/00095 Jan. 14, 1993 which is a continuation of Ser. No. 836,645, Feb. 13, 1992, abandoned.

[51] Int. Cl.$^6$ .................. A61K 31/535; C07D 498/04
[52] U.S. Cl. ..................... 514/230.2; 544/101
[58] Field of Search .................. 544/101; 514/230.2

[56] References Cited

U.S. PATENT DOCUMENTS

| | | | |
|---|---|---|---|
| 4,134,974 | 1/1979 | Melloni et al. | 424/248.54 |
| 4,774,245 | 9/1988 | Wätjen et al. | 514/250 |
| 4,873,244 | 10/1989 | Wätjen et al. | 514/250 |
| 4,902,686 | 2/1990 | Wätjen et al. | 214/250 |
| 4,968,682 | 11/1990 | Hansen et al. | 514/250 |
| 4,999,354 | 3/1991 | Hansen et al. | 514/250 |

FOREIGN PATENT DOCUMENTS

| | | | |
|---|---|---|---|
| 220845 | 5/1987 | European Pat. Off. | C07D 487/04 |
| 2043637 | 10/1980 | United Kingdom | C07D 471/04 |

OTHER PUBLICATIONS

Danswan, G. W. et al., "Synthesis and Reactions of Some Novel Imidazobenzoxazines and Related Systems," J. C. S. Perkin I, 1049–1058 (1982).

*Primary Examiner*—Philip I. Datlow
*Attorney, Agent, or Firm*—Donald L. Corneglio

[57] ABSTRACT

Imidazo-benzoxazines of Formula (I) and pharmaceutically acceptable salts thereof.

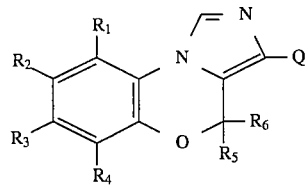

where Q is selected from (A) through (H)

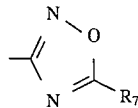

(A)

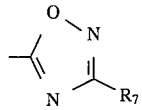

(B)

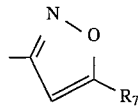

(C)

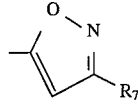

(D)

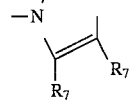

(E)

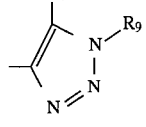

(F)

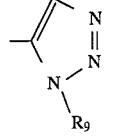

(G)

—$R_{10}$ (H)

or pharmaceutically acceptable salts thereof wherein the R groups are as defined herein. The imidazo-benzoxazines, Formula (I), of the present invention are useful as anxiolytics and sedatives.

9 Claims, No Drawings

4-OXO- AND 4H-IMIDAZO(5,1-C)(1,4)BENZOXAZINES USEFUL AS BENZODIAZEPINE RECEPTOR-BINDING AGENTS

CROSS-REFERENCE TO RELATED APPLICATIONS

This application is a continuation of International patent application No. PCT/US93/00095, filed Jan. 14, 1993; which is a continuation of U.S. Ser. No. 07/836,645, filed Feb. 13, 1992, abandoned.

BACKGROUND OF THE INVENTION

The compounds of the present invention are therapeutically active 4-oxo and 4H-imidazo(5,1-c)(1,4)benzoxazines (I) which are useful in the treatment of central nervous system disorders. These novel compounds are also useful in the preparation of pharmaceutical compositions which can be used, for example, in the treatment of convulsions, as anxiolytics, hypnotics, sedatives, muscle relaxants, antidepressants, for the treatment of panic attacks and treatment of cognitative disorders. It is well known that there are specific sites in the central nervous system of vertebrates that exhibit a high specific affinity for binding 1,4- and 1,5-benzodiazepines. Compounds that have a strong affinity for these receptors are continually being sought in order to therapeutically modify behavior and reduce any undesirable side-effects. The subject compounds are benzoxazines structured compounds with enhanced binding characteristics.

DESCRIPTION OF THE RELATED ART

U.S. Pat. Nos. 4,999,354; 4,968,682; 4,902,686; 4,873,244 and 4,774,245 disclose imidazo(1,5-a)quinoxalines which are compounds similar to the subject compound except that there is an oxygen atom in the heterocyclic ring (i.e., benzoxazine). European Patent Application, Publication No. 0220845, published May 6, 1987, discloses imidazole ring structures which can have the oxygen containing heterocyclic ring; however, they do not disclose any substitution on the benzene ring or oxazine ring.

U.S. Pat. No. 4,134,974 discloses imidazo-benzoxazine structures; however, there is no substitution at the 3-position of the imidazo ring. Danswan, G. W., et al., "Synthesis and Reaction of Some Novel Imidobenzoxazines and Related Systems." J.C.S. Perkins I, 1049–58 (1982) provides a background for synthesis of various related compounds and the subject core ring structure ("2" in the text).

SUMMARY OF INVENTION

In one aspect, the subject invention is directed toward 4-oxo and 4H-imidazo(5,1-c)(1,4)benzoxazinones of Formula (I)

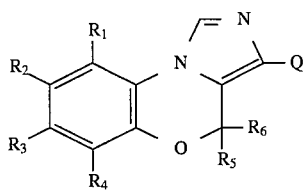

where Q is selected from (A) through (H)

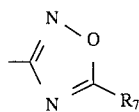 (A)

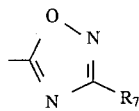 (B)

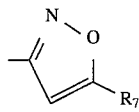 (C)

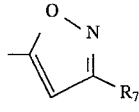 (D)

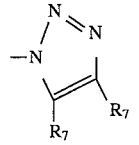 (E)

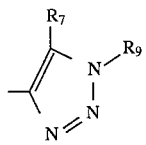 (F)

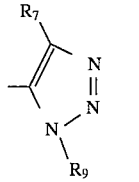 (G)

—$R_{10}$ (H)

or a pharmaceutically acceptable salt thereof, wherein $R_1$, $R_2$, $R_3$ and $R_4$ are independently H, F, Cl, Br, $CF_3$, $C_{1-6}$ alkyl, CN, OH, $OC_{1-6}$ alkyl, —$OC(O)C_{1-6}$ alkyl, $NH_2$, $NH_9$, or $N(R_9)_2$;

$R_5$ and $R_6$ are independently H (with the proviso where $R_1$, $R_2$, $R_3$ and $R_4$ are all H, then only one of $R_5$ or $R_6$ can be H), $C_{1-6}$ alkyl, OH, $CF_3$, OCO—$C_{1-6}$alkyl, OCO—$C_{6-12}$aryl or $R_5$ and $R_6$ together are =O;

$R_7$ is independently H, F, Cl, Br, I, CN, $CF_3$, $C_{1-6}$ alkyl, —$CH_2CH_2CF_3$, —$CH_2CH(CF_3)CH_3$, $C_{3-7}$ cycloalkyl (optionally, substituted with F, Cl, Br, $C_{1-6}$ alkyl, OH or $NH_2$), $C_{1-6}$ alkyl-$C_{3-7}$ cycloalkyls (optionally, substituted with F, Cl, Br, $C_{1-6}$ alkyl, OH or $NH_2$), $C_{6-12}$ aryl, hetero-$C_{6-12}$ aryl, $C_{1-6}$ alkyl-$C_{6-12}$ aryl, $C_{1-6}$ alkyl hetero-$C_{6-12}$ aryl, —$(CH_2)_n$—$OR_9$, —$(CH_2)_n$—$SR_9$, —$(CH_2)_n$—$S(O)_yR_8$, —$(CH_2)_n$—$N(R_9)_2$, —$(CH_2)_n$—$N(O)R_8$, —$(CH_2)_mC(R_8)_2$—$(CH_2)_nOR_9$, —$(CH_2)_mC(R_8)_2$—$(CH_2)_nCHO$, —$(CH_2)_mC(R_8)_2$—$(CH_2)_nCO_2R_8$, —$(CH_2)_m C(R_8)_2—(CH_2)_n CON(R_9)_2$,
—$(CH_2)_m C(R_8)_2—(CH_2)_n SR_9$,
—$(CH_2)_m C(R_8)_2—(CH_2)_n S(O)_y R_8$,
—$(CH_2)_m C(R_8)_2—(CH_2)_n N(R_9)_2$,
—$(CH_2)_m—O—(CH_2)_n—R_9$,
—$(CH_2)_m—S—(CH_2)_n—R_9$,
—$(CH_2)_m—S(O)_y—(CH_2)_n—R_8$,
—$(CH_2)_m—CO—(CH_2)_n—OR_8$,
—$(CH_2)_m—CO—(CH_2)_n—CH_2—OR_8$,
—$(CH_2)_m—CO—(CH_2)_d—SR_9$,
—$(CH_2)_m—CO—(CH_2)_d—S(O)_y R_8$,
—$(CH_2)_m—CO—(CH_2)_n—N(R_9)_2$,
—$(CH_2)_m—CO—(CH_2)_n—C_{1-6}$ alkyl, —$C_{6-12}$ aryl or —$C_{6-12}$ heteroaryl,
—$(CH_2)_m—CHOH—(CH_2)_d—OR_9$,
—$(CH_2)_m—CHOH—(CH_2)_d—SR_9$,
—$(CH_2)_m—CHOH—(CH_2)_d—S(O)_y R_8$,
—$(CH_2)_m—CHOH—(CH_2)_d—N(R_9)_2$,
—$(CH_2)_m—CHOH—(CH_2)_n—C_{1-6}$ alkyl, —$C_{6-12}$ aryl or hetero-$C_{6-12}$ aryl, 2-, 3-tetrahydrofuran (optionally, substituted with $C_{1-6}$ alkyl, OH, or $C_{6-12}$ aryl), 2-, 3-tetrahydrothiophene (sulfone or sulfoxide) (optionally substituted with $C_{1-6}$ alkyl, OH, or $C_{6-12}$ aryl), or

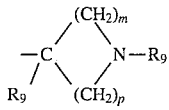

$R_8$ is H, $C_{1-6}$ alkyl, $C_{6-12}$ aryl, $C_{1-6}$ alkyl-$C_{6-12}$ aryl or $C_{1-6}$ alkyl-hetero-$C_{6-12}$ aryl;

$R_9$ is independently H, $C_{1-6}$ alkyl, $C_{6-12}$ aryl, $C_{1-6}$ alkyl-$C_{6-12}$ aryl, $C_{1-6}$ alkyl-$C_{6-12}$ heteroaryl, —C(O)—$R_8$, —C(O)N($R_8$)$_2$ or —$(CH_2)_n$—N($R_8$)$_2$;

$R_{10}$ is $R_7$,
 —$CO_2 R_8$,
 —$CON(R_9)_2$,
 —$CH=CHR_9$,
 —$CH=CHCH(OH)R_9$,
 —$CH=CHCO_2 R_8$,
 —$CH=CHCON(R_9)_2$,
 —$CH=CH(CH_2)_n OR_9$,
 —$CH=CH(CH_2)_n SR_9$,
 —$CH=CH(CH_2)_n S(O)_y R_9$,
 —$CH=CH(CH_2)_n N(R_9)_2$,
 —$C\equiv CR_9$,
 —$C\equiv CCH(OH)R_9$,
 —$C\equiv CCO_2 R_8$,
 —$C\equiv CCON(R_9)_2$,
 —$C\equiv C(CH_2)_n OR_9$,
 —$C\equiv C(CH_2)_n S(O)_y R_8$, or
 —$C\equiv C(CH_2)_n N(R_9)_2$; and
m=0–3, n=0–5, p=1–3, y=1–2, d=1–3.

In another aspect, the subject invention is directed toward a method for treating central nervous system disorders associated with the benzodiazepine receptors in a subject in need of such treatment comprising administering to the subject a therapeutically-effective amount of a Formula I compound for alleviation of such disorder. Typically, the compound of Formula I is administered in the form of a pharmaceutical composition comprising a pharmaceutically-acceptable carrier or diluent.

In yet another aspect, the subject invention is directed toward a pharmaceutical composition for treating central nervous system disorders associated with the benzodiazepine receptors comprising an effective amount of a compound of Formula I with a pharmaceutically-acceptable carrier or diluent.

DETAILED DESCRIPTION OF THE INVENTION

The present invention is directed toward novel compounds developed around the imidazo-benzoxazinone core having binding affinity for the benzodiazepine receptors and therefore have important therapeutic value in the treatment of central nervous system disorders such as anticonvulsants, anxiolytics, hypnotics and nootropics.

The compounds of the invention are as defined by Formula I, above. Preferred compounds are substituted at the C-3 position of the imidazole ring (Q) with either an ester or substituted oxadiazole system. Preferably, the C-4 position on the oxazine ($R_{5,6}$) can be substituted with hydrogen, alkyl, hydroxyl or, taken together to form a carbonyl group. Preferably, the aromatic ring ($R_{1-4}$) can be substituted with hydrogen, alkyl, $CF_3$, fluorine, chlorine, cyano, hydroxyl, alkoxyl and amino (and derivatives thereof), more preferably one of the halogens F or Cl. The most potent benzodiazepine receptors binding compounds are where $R_3$ is F; $R_{5,6}$ are H; Q is 5-cyclopropyl-1,2,4-oxadiazol-3-yl and where $R_3$ is F; $R_{5,6}$ are H; and Q is $CO_2$Et.

"Alkyl" are one to six carbon atoms such as methyl, ethyl, propyl, butyl, pentyl, hexyl, and isomeric forms thereof.

"Aryl" are six to twelve carbon atoms such as phenyl, α-naphthyl, β-naphthyl, m-methylphenyl, p-trifluoromethylphenyl and the like. The aryl groups can also be substituted with one to 3 hydroxy, —$OR_8$, —$OCOR_8$, fluoro, chloro, or bromo groups.

"Cycloalkyl" are three to seven carbon atoms such as cyclopropyl, cyclobutyl, cyclopentyl and cyclohexyl.

"Alkyl-aryl" are alkyl chains of one to six carbon atoms and isomeric forms thereof which are substituted with aryl groups of six to twelve carbon atoms as described above.

"Heteroaryl" are six to twelve carbon atoms aryls, as described above, containing the heteroatoms nitrogen, sulfur or oxygen. Heteroaryls are pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pryidazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-indolyl, 3-indolyl, 3-indazolyl, 2-benzoxazolyl, 2-benzothiazolyl, 2-benzimidazolyl, 2-benzofuranyl, 3-benzofuranyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 1-purinyl, 3-isothiazolyl, 4-isothiazolyl, 5-isothiazolyl.

Since the subject imidazo-benzoxazines (I) are amines, many do not form salts, but some do. If salts can be made, they are preferred because of their increased water solubility. When salts of the imidazo-benzoxazines (I) are made they are produced by reaction with acids of sufficient strength.

Pharmaceutically acceptable salts include salts of both inorganic and organic acids. The pharmaceutically acceptable salts are preferred over the corresponding free amines since they produce compounds which are more water soluble. The preferred pharmaceutically acceptable salts include salts of the following acids: methanesulfonic, hydrochloric, hydrobromic, sulfuric, phosphoric, nitric, benzoic, citric, tartaric, fumaric or maleic.

The imidazo-benzoxazines (I) are active orally or parenterally. Orally the imidazo-benzoxazines (I) can be given in solid dosage forms such as tablets or capsules, or can be given in liquid dosage forms such as elixirs, syrups or suspensions as is known to those skilled in the art. It is preferred that the imidazo-benzoxazines (I) be given in solid dosage form and that it be a tablet.

For anxiolytic effect the imidazo-benzoxazines (I) should be given in the amount of about 0.25 mg to about 100 mg/person, one to three times a day. Preferably, about 10 to about 50 mg/day in divided doses.

For sedative/hypnotic effect the imidazo-benzoxazines (I) should be given in the amount of about 0.25 mg to about 500 mg/person, preferably at bedtime or when sedation is needed. It is preferred the sedative/hypnotic dose be from about 10 to about 100 mg/person.

The exact dosage and frequency of administration depends on the particular imidazo(1,5-a)quinoxaline (I) used, the particular condition being treated, the severity of the condition being treated, the age, weight, general physical condition of the particular patient, other medication the individual may be taking as is well known to those skilled in the art and can be more accurately determined by measuring the blood level or concentration of the imidazo-benzoxazines (I) in the patient's blood and/or the patient's response to the particular condition being treated.

Thus, the subject compounds, along with a pharmaceutically-acceptable carrier, diluent or buffer, can be administrated in a therapeutic or pharmacological amount effective to alleviate the central nervous system disorder with respect to the physiological condition diagnosed. The compounds can be administered intravenously, intramuscularly, topically, transdermally such as by skin patches, buccally or orally to man or other vertebrates.

The compositions of the present invention can be presented for administration to humans and other vertebrates in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other insert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

The pharmaceutical properties of the invention are demonstrated by determining their ability to displace radioactive labelled flunitrazepam from benzodiazepine receptors. In the following Table, Ki values are shown for Examples 1–19 which include comparative compounds 1, 7, 9 and 11, which are not compounds of the subject invention but are structurally similar.

The Ki value is determined from a concentration response curve obtained in the presence and absence of a fixed concentration of competitive antagonist, flunitrazepam. Comparison of the agonist concentrations required to produce identical degrees of effect reveals the Ki. The lower Ki value indicates a higher affinity for benzodiazepine.

TABLE

| Example | Q | $R_7$ | $R_3$ | $R_4$ | $R_{5,6}$ | Ki |
|---|---|---|---|---|---|---|
| $1^1$ | A | cyclopropyl | H | H | H,H | 39.73 |
| 2 | A | cyclopropyl | $NHCO_2C_4H_8$ | H | H,H | $1 \times 10^4$ |
| 3 | A | cyclopropyl | H | H | $-OCO-Ph$ | 121.03 |
| 4 | A | cyclopropyl | H | H | $-OH$ | 117.63 |
| 5 | A | cyclopropyl | $NH_2$ | H | H,H | 65.37 |
| 6 | A | cyclopropyl | $NHCO_2C_4H_9$ | H | $-OCO-Ph$ | $1 \times 10^4$ |
| $7^1$ | $CO_2C_2H_5$ | — | H | H | H,H | 59.58 |
| 8 | A | cyclopropyl | $NHOCCF_3$ | H | H,H | $1 \times 10^4$ |
| $9^1$ | B | cyclopropyl | H | H | H,H | 72.64 |
| 10 | A | cyclopropyl | H | H | $=O$ | 655.80 |
| $11^1$ | $CO_2t-C_4H_9$ | — | H | H | H,H | 69.91 |
| 12 | A | cyclopropyl | H | H | $CH_3$ | 113.97 |
| 13 | A | cyclopropyl | F | H | H,H | 8.56 |
| 14 | A | cyclopropyl | H | H | $CH_3,CH_3$ | 67.14 |
| 15 | $CO_2C_2H_5$ | — | F | H | H,H | 4.59 |

TABLE-continued

| Example | Q | $R_7$ | $R_3$ | $R_4$ | $R_{5,6}$ | Ki |
|---|---|---|---|---|---|---|
| 16 | $CO_2t$-$C_4H_9$ | — | F | H | H,H | 32.40 |
| 17 | A | t-$C_4H_9$ | F | H | H,H | 442,84 |
| 18 | B | —N(CH$_3$)$_2$ | F | H | H,H | 153.76 |
| 19 | $CO_2t$-$C_4H_9$ | — | F | CN | H,H | 4.60 |

Note: $R_1$,$R_2$ are both hydrogen.
[1]Not compounds of the subject invention, used for comparison.

The imidazo-benzoxazines (I) are produced by a number of processes depending on the variable substituents involved. Processes to prepare the imidazo-benzoxazines (I) are generally routine in the art and are demonstrated in the Examples which follow.

When the final product is other than a 1-substituted cycloalkyl, the compound will contain an asymmetric center and therefore produce two enantiomers one "S" and the other "R", either of which can be (+/d) and the other (−/l). Both enantiomers (+) and (−) are useful in the same way as the optically impure (racemic, ±) mixture. Hence, they may be utilized in the racemic form without separating them. However, if it is desired to utilize one of the enantiomers, two methods are available to produce optically pure forms (see for example, Optical Resolution Procedures for Chemical Compounds, Vol 1,: Amines and Related Compounds, Paul Newman, Optical Resolution Information Center, Manhattan College, Riverdale, N.Y., 10471; 1978).

EXAMPLES

The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

(Not a compound of this invention.) The following preparation is illustrative of a method for preparing the basic core heterocyclic structure for Formula I.

3-(5-Cyclopropyl-1,2,4-oxadiazol-3-yl)-4H-imidazo(5,1-c)(1,4)benzoxazine 2H-1,4-benzoxazine-3-one (2a)

Chloroacetyl chloride (2.82 g, 1.95 ml, 25 mmol) in dry ether (25 ml) was added dropwise over 15 minutes to a stirring solution of 2-aminophenol (5.45 g, 50 mmol) in dry ether (85 ml). After sitting for 2 h, the reaction mixture was filtered rinsing with ether. The filtrate was evaporated to afford 6.5 g of crude product. Recrystallization from ether/hexane afforded 3.48 g (75% yield) of crystalline Intermediate A. Mp 134°–5° C.;

Intermediate A (3.4 g, 18.5 mmol) was stirred in refluxing 0.2M NaHCO$_3$ (185 ml, 37 mmol) for 2 h. After cooling, the solution was acidified to pH 5.0 with 2N HCl and transferred to a separatory funnel with water and ether. Extracting with ether (2×), washing the combined organic layers with brine and drying over MgSO$_4$ afforded 2.84 g of crude product after evaporation of the solvent. Recrystallization from ether afforded 2.30 g (83%) crystalline compound 2a. Mp 167°–70° C.

Potassium t-butoxide (1M in THF, 4.35 ml, 4.35 mmol) was added to a solution of 2a (0.6 g, 4 mmol) in THF (16 ml) stirring under nitrogen at 0° C. in a flame dried 3-neck round bottom flask. After stirring at ambient temperature for 30 minutes, the reaction was cooled to −20° C. and diethylchlorophosphate (0.75 ml, 5.2 mmol) was added. After stirring at ambient temperature for 45 minutes, the reaction was cooled to −78° C. and the isocyanate (0.65 g, 4.36 mmol) in THF (1.5 ml) was added followed by potassium t-butoxide (1M in THF, 4.35 ml, 4.35 mmol) whereupon the reaction turned red. After stirring at ambient temperature for 3 h, the reaction mixture was transferred to a separatory funnel containing EtOAc/1N HCl. Extraction with EtOAc (2×), washing the combined organic layers with brine, and drying over MgSO$_4$ afforded 2.75 g of crude product after evaporation of the solvent. Flash chromatography over silica gel (180 g, 0–15% EtOAc/CH$_2$Cl$_2$) afforded 0.97 g (87%) of Example compound 1. An analytical sample was prepared by recrystallization from EtOAc/hexane. Mp 138°–9.5° C.

EXAMPLE 2

7-(Amino(t-butoxycarbonyl))-3-(5-cyclopropyl-1,2,4-oxadiazol-3-yl)-4H-imidazo(5,1-c)(1,4)benzoxazine N-(2-Hydroxy-4-nitrophenyl)-2-chloroacetamide Chloroacetyl chloride (5.7 g, 3.9 ml, 50 mmol) in dry ether (50 ml) was added dropwise over 15 minutes to a stirring solution of 2-amino-5-nitrophenol (1b, 15.4 g, 100 mmol) in dry ether (170 ml). After refluxing for 3 days, the reaction mixture was evaporated and 20% EtOAc/CH$_2$Cl$_2$ with 2% MeOH was added. After filtration, the filtrate was flash chromatographed over silica gel (300 g, 20% EtOAc/CH$_2$Cl$_2$) to afford 0.54 g of intermediate B. Recrystallized from EtOAc/hexane. Mp 228°–32° C.

7-Nitro-2H-1,4-benzoxazine-3-one (2b)

The amide intermediate B (3.24 g, 14 mmol) was stirred in refluxing 0.2M NaHCO$_3$ (75 ml, 15 mmol) for 2 h. After cooling, the solution was acidified to pH 5.5 with 2N HCl and transferred to a separatory funnel with water and EtOAc. Extracting with EtOAc (2×), washing the combined organic layers with brine and drying over MgSO$_4$ afforded 3.8 g of crude product after evaporation of the solvent. Flash chromatography over silica gel (600 g, 10–25% EtOAc/CH$_2$Cl$_2$) afforded 1.61 g (59%) of compound 2b. An analytical sample was prepared by recrystallization from CH$_2$Cl$_2$. Mp 226°–9° C.

7-Amino-2H-1,4-benzoxazine-3-one (2c)

A suspension of 10% palladium on carbon (0.24 g) and 2b (2.39 g, 12.3 mmol) in methanol (65 ml) was shaken under 25 lbs H$_2$ in a Parr hydrogenation apparatus. After 3 h, the catalyst was filtered and the filtrate evaporated to afford 1.63 g (81%) of compound 2c. An analytical sample was recrystallization from MeOH/hexane. Mp 216°–7° C.

7-t-Butoxycarbonylamino-2H-1,4-benzoxazine-3-one (2d)

Di-t-butyldicarboxylate (2.5 g, 11.4 mmol) in THF (20 ml) was slowly added to a solution of compound 2c (1.63 g, 10 mmol) in THF (50 ml) stirring at 0° C. After stirring at ambient temperature for 3 days, the reaction was evaporated in vacuo to afford 3.11 g of crude product. Flash chromatography over silica gel (250 g, 10% EtOAc/CH$_2$Cl$_2$) afforded 2.32 g (87%) of compound 2d. An analytical sample was prepared by recrystallization from EtOAc. Mp 200°–3° C.

3-(5-Cyclopropyl-1,2,4-oxadiazol-3-yl)-7-t-butoxycarbonylamino-5-imidazo(1,5-a)benzoxazine (Example compound 2)

Potassium t-butoxide (1M in THF, 6.0 ml, 6.0 mmol) was added to a solution of compound 2d (1.5 g, 5.7 mmol) in THF (22 ml) stirring under nitrogen at 0° C. in a flame dried 3-neck round bottom flask. After stirring at 10° C. for 30 minutes, the reaction was cooled to −20° C. and diethylchlorophosphate (1.0 ml, 7.2 mmol) was added. After stirring at 0° C. for 50 minutes, the reaction was cooled to −78° C. and the isocyanate (0.89 g, 6.0 mmol) in THF (1.7 ml) was added followed by potassium t-butoxide (1M in THF, 6.0 ml, 6.0 mmol). After stirring at ambient temperature for 1 h, the reaction mixture was transferred to a separatory funnel containing EtOAc/0.5N HCl. Extraction with EtOAc (2×), washing the combined organic layers with brine, and drying over MgSO$_4$ afforded 2.7 g of crude product after evaporation of the solvent. Flash chromatography over silica gel (250 g, 5%–50% EtOAc/CH$_2$Cl$_2$) afforded 1.77 g (79%) of Example compound 2. An analytical sample was recrystallization from EtOAc. Mp 219°–23° C.

EXAMPLE 3

3-(5-Cyclopropyl-1,2,4-oxadiazol-3-yl)-4-(benzoyloxy)-4H-imidazo(5,1-c)(1,4)benzoxazine t-Butylperbenzoic acid (1.2 ml, 6.2 mmol in acetonitrile (2 ml) was added to a stirring solution of Example compound 1 (1.12 g, 4 mmol) and CuBr (2 mg). At 1.5 h and 4 h additional aliquots of CuBr (2 mg) were added to the refluxing reaction mixture. After 5 h, the reaction was evaporated and the residue transferred to a separatory funnel with EtOAc/H$_2$O. Extraction with EtOAc (3×), washing the combined organic layers with saturated NaHCO$_3$ and brine, and drying over MgSO$_4$ afforded 2.61 g of crude product. Flash chromatography over silica gel (150 g, 5% acetone/CH$_2$Cl$_2$) afforded 1.08 g (67%) of Example compound 3. An analytical sample was prepared by recrystallization from EtOAc/hexane. Mp 165°–7° C.

EXAMPLE 4

3-(5-Cyclopropyl-1,2,4-oxadiazol-3-yl)-4-hydroxy-4H-imidazo(5,1-c)(1,4)benzoxazine 3-(5-Cyclopropyl-1,2,4-oxadiazol-3-yl)-4-(benzoyloxy)-4H-imidazo(5,1-c)(1,4)benzoxazine, Example compound 3 (0.88 g), was placed in methanol (44 mL). To that solution was added sodium methoxide (0.24 g) and stirring continued for 3.75 hours. The reaction was evaporated to dryness and triturated with water. Recrystallization from methanol afforded 0.53 g (81%) of the title compound. Mp 230°–4° C.

EXAMPLE 5

7-Amino-3-(5-cyclopropyl-1,2,4-oxadiazol-3-yl)-4H-imidazo(5,1-c)(1,4)benzoxazine Gaseous HCl was bubbled through a solution of Example compound 2 (2.0 g, 5.06 mmol) in EtOAc (150 ml) until it was saturated. After sitting at ambient temperature for 4 h, 1N NaOH was added with stirring until the pH of the aqueous layer was 10. Extraction with EtOAc (2×), washing the combined organic layers with brine, and drying over MgSO$_4$ afforded 1.56 g of crude material after evaporation of the solvent. Recrystallization from CH$_2$Cl$_2$/hexane afforded 1.24 g (83%) of crystalline Example compound 5. Mp 201°–4° C.

EXAMPLE 6

7-(Amino(t-butoxycarbonyl))3-(5-cyclopropyl-1,2,4-oxadiazol-3-yl)-4-(benzoyloxy)-4H-imidazo(5,1-c)(1,4)benzoxazine t-Butylperbenzoic acid (0.76 ml, 3.9 mmol) in acetonitrile (1 ml) was added to a stirring solution of Example compound 2 (1.0 g, 2.5 mmol) and CuBr (1 mg). After refluxing for 5 h, the reaction was evaporated and the residue transferred to a separatory funnel with EtOAc/H$_2$O. Extraction with EtOAc (3×), washing the combined organic layers with saturated NaHCO$_3$ and brine, and drying over MgSO$_4$ afforded 1.7 g of crude product. Flash chromatography over silica gel (120 g, 5–10% acetone/CH$_2$Cl$_2$) afforded 0.69 g (53%) of Example compound 6. An analytical sample was prepared by recrystallization from CH$_2$Cl$_2$/hexane. Mp 230°–5° C.

EXAMPLE 7

(Not a compound of this invention.) The following preparation is illustrative of a procedure useful in preparing compounds of this invention.

Ethyl 4H-imidazo(5,1-c)(1,4)benzoxazine-3-carboxylate

Potassium t-butoxide (1M in THF, 34.8 ml) was added to a solution of 2H-1,4-benzoxazine-3-one (2a; 4.8 g) in THF (27 ml) stirring under nitrogen at 0° C. in a flame dried 3-neck round bottom flask. After stirring at ambient temperature for 30 minutes, the reaction was cooled to −20° C. and diethylchlorophosphate (41.6 ml) was added. After stirring at ambient temperature for 45 minutes, the reaction was cooled to −78° C. and the ethyl isocyanate (4.14 g) in THF (2.5 ml) was added followed by potassium t-butoxide (1M in THF, 7.24 ml) whereupon the reaction turned red. After stirring at ambient temperature for 3 h, the reaction mixture was transferred to a separatory funnel containing EtOAc/1N HCl. Extraction with EtOAc (2×), washing the combined organic layers with brine, and drying over MgSO$_4$ afforded 12.1 g of crude product after evaporation of the solvent. Flash chromatography over silica gel (600 g, 5% acetone/CH$_2$Cl$_2$) afforded 7.1 g (91%) of Example Compound 7. Mp 135°–7° C.

EXAMPLE 8

7-(Amino(trifluoroacetyl))-3-(5-cyclopropyl-1,2,4-oxadiazol-3-yl)-4H-imidazo(5,1-c)(1,4)benzoxazine Example compound 5, (7-amino-3-(5-cyclopropyl-1,2,4-oxadiazol-3-yl)-4H-imidazo(5,1-c)(1,4)benzoxazine; 0.295 g) was dissolved in methylene chloride (5 mL) and cooled to 0° C. To that solution was added pyridine (0.089 mL) followed by trifluoroacetic anhydride (0.231 g). That mixture was stirred for 2 hours. The reaction was transferred to a separatory funnel and EtOAc/H$_2$O was added. The organic layer was dried (MgSO$_4$) and solvent removed in vacuo to yield 0.39 g of product. Recrystallization from acetone/hexane afforded 0.273 g of Example compound 8. Mp 242°–4° C.

EXAMPLE 9

Scheme Ia (Not a compound of this invention.) This invention is illustrative of another procedure for preparing compounds of this invention.

3-(3-Cyclopropyl-1,2,4-oxadiazol-5-yl)-4H-imidazo(5,1-c)(1,4)benzoxazine

Sodium hydride (50% oil dispersion, 0.51 g) was added to THF (90 mL) under nitrogen and at room temperature. Cyclopropyl carboxamide oxime (1.10 g) was added to the above mixture followed by ethyl 4H-imidazo(5,1-c)(1,4)benzoxazine-3-carboxylate (2.44 g) in a mixture of THF (15 mL) and DMF (40 mL). That mixture was stirred at room temperature for 3.5 h and then quenched by the addition of 0.63 mL of HOAc. That mixture was stirred for 10 minutes and then filtered through celite. The filtrate was evaporated and transferred to a separatory funnel and extracted with methylene chloride. The organic solvent was evaporated and the resulting oil triturated with water to yield 1.5 g of crude product. That material was washed with hot EtOAc, chromatographed over silica gel (eluted with EtOAc) to afford 0.53 g of Example compound 9. Mp 169°–73° C.

EXAMPLE 10

3-(5-Cyclopropyl-1,2,4-oxadiazol-3-yl)-4-oxo-4H-imidazo(5,1-c)(1,4)benzoxazine 2-Methyl-2-butene (1.5 mL) was added to a butanol (8 mL) solution of the compound of Example 4 (0.296 g) and that mixture cooled to 5°–10° C. NaClO$_2$ (0.16 g) in 1.6 mL of phosphate buffer (adjusted to pH=3.5) was added to the above reaction mixture. The reaction was stirred at room temperature for 4 days and then quenched by the addition of brine and 5% HCL/EtOAc. The organic layer was separated, dried (MgSO$_4$) and solvent removed in vacuo to yield 0.26 g of an intermediate hydroxy acid. Treatment of that acid with p-toluene sulfonic acid (5 mg) in refluxing toluene for 4 hours followed by evaporation of solvent and silica gel chromatography afforded 124 mg (42%) of the title compound of Example 10. Mp 234°–6° C.

EXAMPLE 11

(Not a compound of this invention.) This example is illustrative of another procedure for preparing compounds of this invention.

Tert-butyl 4H-imidazo(5,1-c)(1,4)benzoxazine-3-carboxylate

Potassium t-butoxide (1M in THF, 7.24ml) was added to a solution of 2H-1,4-benzoxazine-3-one (2a; 1.0 g) in THF (27 ml) stirring under nitrogen at 0° C. in a flame dried 3-neck round bottom flask. After stirring at ambient temperature for 30 minutes, the reaction was cooled to −20° C. and diethylchlorophosphate (1.25 ml) was added. After stirring at ambient temperature for 45 minutes, the reaction was cooled to −78° C. and the tert-butylisocyanate (1.10 g) in THF (2.5 ml) was added followed by potassium t-butoxide (1M in THF, 7.24ml) whereupon the reaction turned red. After stirring at ambient temperature for 3 h, the reaction mixture was transferred to a separatory funnel containing EtOAc/1N HCl. Extraction with EtOAc (2×), washing the combined organic layers with brine, and drying over MgSO$_4$ afforded 3.22 g of crude product after evaporation of the solvent. Flash chromatography over silica gel (180 g, 5% acetone/CH$_2$Cl$_2$) afforded 1.40 g (77%) of Example Compound 11. Mp 119°–23° C.

EXAMPLE 12

3-(5-Cyclopropyl-1,2,4-oxadiazol-3-yl)-4-methyl-4H-imidazo(5,1-c)(1,4)benzoxazine Using the standard procedure as outlined in Example 1 and using 2-methyl-2H-1,4-benzoxazine-3-one (2f) and the 5-cyclopropyl-1,2,4-oxadiazol-3-yl isocyanate the title Example 12 compound was prepared. Mp 162° C.

EXAMPLE 13

3-(5-Cyclopropyl-1,2,4-oxadiazol-3-yl)-7-fluoro-4H-imidazo(5,1-c)(1,4)benzoxazine Using the standard procedure as outlined in Example 1 and using 6-fluor-2H-1,4-benzoxazine-3-one and the 5-cyclopropyl-1,2,4-oxadiazol-3-yl isocyanate the title Example 13 compound was prepared. Mp 182°–4° C.

EXAMPLE 14

3-(5-Cyclopropyl-1,2,4-oxadiazol-3-yl)-4,4-dimethyl-4H-imidazo(5,1-c)(1,4)benzoxazine Using the standard procedure as outlined in Example 1 and using 2,2-dimethyl-2H-1,4-benzoxazine-3-one (2f) and the 5-cyclopropyl-1,2,4-oxadiazol-3-yl isocyanate the title Example 14 compound was prepared. Mp 155°–6° C.

EXAMPLE 15

Ethyl 7-fluoro-4H-imidazo(5,1-c)(1,4)benzoxazine-3-carboxylate

Using the standard procedure as outlined in Example 7 and using 6-fluor-2H-1,4-benzoxazine-3-one the title Example 15 compound was prepared. Mp 179°–80° C.

EXAMPLE 16

Tert-butyl 7-fluoro-4H-imidazo(5,1-c)(1,4)benzoxazine-3-carboxylate

Using the standard procedure as outlined in Example 7 and using 6-fluor-2H-1,4-benzoxazine-3-one and the tert-butyisocyanate the title Example 16 compound was prepared. Mp 133°–4° C.

EXAMPLE 17

3-(5-Tert-butyl-1,2,4-oxadiazol-3-yl)-7-fluoro-4H-imidazo(5,1-c)(1,4)benzoxazine Using the standard procedure as outlined in Example 1 and using 6-fluor-2H-1,4-benzoxazine-3-one and the 5-tert-butyl-1,2,4-oxadiazol-3-yl isocyanate the title Example 17 compound was prepared. Mp 133°–5° C.

EXAMPLE 18

3-(3-dimethylamino-1,2,4-oxadiazol-5-yl)-7-fluoro-4H-imidazo(5,1-c)(1,4)benzoxazine Using the standard procedure as outlined in Example 1 and using 7-fluor-2H-1,4-benzoxazine-3-one and the 3-dimethylamino-1,2,4-oxadiazol-5-yl isocyanate the title Example 18 compound was prepared. Mp 239°–40° C.

EXAMPLE 19

Tert-butyl 6-cyano-7-fluoro-4H-imidazo(5,1-c)(1,4)benzoxazine-3-carboxylate

Using the standard procedure as outlined in Example 7 and using 5-cyano-6-fluor-2H-1,4-benzoxazine-3-one and the tert-butyisocyanate the title Example 19 compound was prepared. Mp 250°–3° C.

EXAMPLE 20

Scheme VI 3-(3-Cyclopentyl-1,2,4-oxadiazol-5-yl)-7-fluoro-4H-imidazo(5,1-c)(1,4)benzoxazine Using the standard procedure as outlined in Example 1 and using 6-fluor-2H-1,4-benzoxazine-3-one and the 5-cyclopentyl-1,2,4-oxadiazol-3-yl isocyanate the title Example 20 compound was prepared. Mp 134°–5° C.

What is claimed:

1. A compound of formula (I)

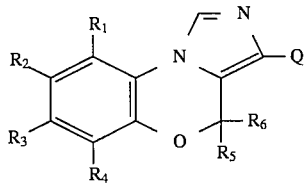

(I)

where Q is selected from (A) through (C)

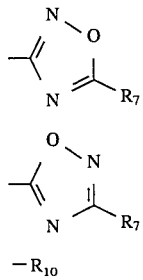

or a pharmaceutically acceptable salt thereof wherein $R_1$, $R_2$ and $R_4$ are independently H, F, Cl, Br, $CF_3$, $C_{1-6}$ alkyl, CN, OH, $OC_{1-6}$ alkyl, $-OC(O)C_{1-6}$ alkyl, $NH_2$, $NHR_9$ or $N(R_9)_2$;

$R_3$ is F;

$R_5$ and $R_6$ are independently H $C_{1-6}$ alkyl, OH, $CF_3$, $OCO-C_{1-6}$alkyl, $-OCO-C_{6-12}$aryl or $R_5$ and $R_6$ together are =O;

$R_7$ is H, F, Cl, Br, I, CN, $CF_3$, $C_{1-6}$ alkyl, $-CH_2CH_2CF_3$, $-CH_2CH(CF_3)CH_3$; $C_{3-7}$ cycloalkyl (optionally, substituted with F, Cl, Br, $C_{1-6}$ alkyl, OH or $NH_2$), $C_{1-6}$ alkyl-$C_{3-7}$ cycloalkyls (optionally, substituted with F, Cl, Br, $C_{1-6}$ alkyl, OH or $NH_2$), or $-(CH_2)_n-N(R_9)_2$, $-(CH_2)_n-N(O)R_8$, or

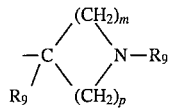

$R_8$ is H, $C_{1-6}$ alkyl, $C_{6-12}$ aryl, $C_{1-6}$ alkyl-$C_{6-12}$ aryl or $C_{1-6}$ alkyl-hetero-$C_{6-12}$ aryl;

$R_9$ is independently H, $C_{1-6}$ alkyl, $C_{6-12}$ aryl, $C_{1-6}$ alkyl-$C_{6-12}$ aryl, $C_{1-6}$ alkyl-$C_{6-12}$ heteroaryl, $-C(O)-R_8$, $-C(O)N(R_8)_2$ or $-(CH_2)_n-N(R_8)_2$;

$R_{10}$ is $-CO_2R_8$ or $-CON(R_9)_2$; and m=0–3, n=0–5, p=1–3.

2. The compound of claim 1 where Q is structure A.
3. The compound of claim 1 where $R_1$, $R_2$ and $R_4$ are H.
4. The compound of claim 1 where $R_5$ and $R_6$ are H.
5. The compound of claim 1 which is
   a) 3-(5-Cyclopropyl-1,2,4-oxadiazol-3-yl)-7-fluoro-4H-imidazo(5,1-c)(1,4)benzoxazine;
   b) Ethyl 7-fluoro-4H-imidazo(5,1-c)(1,4)benzoxazine-3-carboxylate;
   c) Tert-butyl 7-fluoro-4H-imidazo(5,1-c)(1,4)benzoxazine-3-carboxylate;
   d) 3-(5-Tert-butyl-1,2,4-oxadiazol-3-yl)-7-fluoro-4H-imidazo(5,1-c)(1,4)benzoxazine;
   e) 3-(3-dimethylamino-1,2,4-oxadiazol-5-yl)-7-fluoro-4H-imidazo(5,1-c)(1,4)benzoxazine;
   f) Tert-butyl 6-cyano-7-fluoro-4H-imidazo(5,1-c)(1,4)benzoxazine-3-carboxylate; or
   g) 3-(3-Cyclopentyl-1,2,4-oxadiazol-5-yl)-7-fluoro-4H-imidazo(5,1-c)(1,4)benzoxazine.

6. A method for treating central nervous system disorders associated with the benzodiazepine receptors in a patient in need of such treatment comprising:

administering to said patient a therapeutically effective amount of a compound of Formula I as defined in claim 1 for alleviation of such disorder.

7. The method of claim 6 wherein the compound is administered in a therapeutically effective amount in the form of a pharmaceutical composition having a pharmaceutically-acceptable carrier or diluent.

8. A pharmaceutical composition for treating central nervous system disorders associated with the benzodiazepine receptors comprising an effective amount of a Formula I compound of claim 1 with a pharmaceutically-acceptable carrier or diluent.

9. The pharmaceutical composition of claim 8 where the compound is present in an amount of from 10 to 100 mg.

* * * * *